United States Patent
Hamm

(10) Patent No.: US 7,613,503 B2
(45) Date of Patent: Nov. 3, 2009

(54) DEVICE WITH INFUSION HOLES FOR IMAGING INSIDE A BLOOD VESSEL

(75) Inventor: Mark Hamm, Lynnfield, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1169 days.

(21) Appl. No.: 10/216,561

(22) Filed: Aug. 9, 2002

(65) Prior Publication Data

US 2004/0030220 A1 Feb. 12, 2004

(51) Int. Cl.
*A61B 6/00* (2006.01)

(52) U.S. Cl. .................. 600/476; 600/407; 600/431; 600/459; 600/463; 600/467; 604/22; 604/103.01; 604/171; 604/508; 604/509

(58) Field of Classification Search ............. 600/463, 600/467, 407, 431, 459, 464, 476; 604/195, 604/508, 22, 103.01, 171, 509, 525; 607/9
See application file for complete search history.

(56) References Cited

U.S. PATENT DOCUMENTS

| | | | |
|---|---|---|---|
| 4,951,677 A | 8/1990 | Crowley et al. | |
| 5,087,244 A | 2/1992 | Wolinsky et al. | 604/53 |
| 5,112,305 A | 5/1992 | Barath et al. | 604/96 |
| 5,152,293 A | 10/1992 | Vonesh et al. | |
| 5,178,151 A * | 1/1993 | Sackner | 600/485 |
| 5,195,985 A * | 3/1993 | Hall | 604/195 |
| 5,318,531 A | 6/1994 | Leone | 604/96 |
| 5,321,501 A | 6/1994 | Swanson et al. | |
| 5,336,178 A | 8/1994 | Kaplan et al. | 604/53 |
| 5,344,402 A | 9/1994 | Crocker | 604/96 |
| 5,454,373 A * | 10/1995 | Koger et al. | 600/463 |
| 5,459,570 A | 10/1995 | Swanson et al. | |
| 5,609,574 A | 3/1997 | Kaplan et al. | 604/53 |
| 5,626,564 A | 5/1997 | Zhan et al. | |
| 5,653,689 A | 8/1997 | Buelna et al. | 604/96 |
| 5,795,318 A * | 8/1998 | Wang et al. | 604/8 |
| 5,833,659 A | 11/1998 | Kranys | 604/96 |
| 5,855,546 A * | 1/1999 | Hastings et al. | 600/3 |
| 5,855,563 A | 1/1999 | Kaplan et al. | 604/49 |
| 5,916,193 A | 6/1999 | Stevens et al. | |
| 5,957,901 A * | 9/1999 | Mottola et al. | 604/264 |

(Continued)

FOREIGN PATENT DOCUMENTS

EP 0 406 901 A1 1/1991

(Continued)

*Primary Examiner*—Brian Casler
*Assistant Examiner*—Baisakhi Roy
(74) *Attorney, Agent, or Firm*—Darby & Darby PC

(57) ABSTRACT

An imaging device such as a catheter has a plurality of infusion holes adapted to infuse liquid into the blood stream while substantially preventing radial jetting. An example imaging catheter includes an elongated member, having distal and proximal ends, an axis, a lumen along the axis, and an outer surface. Preferably, a plurality of infusion holes are defined along the axis of said elongated member between the lumen and the outer surface. The plurality of infusion holes may be tapered from the outer surface to the lumen. Further, the plurality of infusion holes may be angled outwardly toward the proximal end of the elongated member. The size, shape, spacing and configuration of the infusion holes may be varied as desired.

33 Claims, 3 Drawing Sheets

U.S. PATENT DOCUMENTS

| | | | |
|---|---|---|---|
| 6,063,069 A * | 5/2000 | Cragg et al. | 604/508 |
| 6,149,624 A * | 11/2000 | McShane | 604/113 |
| 6,423,081 B1 | 7/2002 | Lee et al. | |
| 6,623,452 B2 * | 9/2003 | Chien et al. | 604/103.01 |
| 2002/0077594 A1 | 6/2002 | Chien et al. | |

FOREIGN PATENT DOCUMENTS

| | | |
|---|---|---|
| JP | 1066612 | 3/1989 |
| JP | 1274772 | 11/1989 |
| JP | 2124128 | 5/1990 |
| JP | 5293074 | 11/1993 |
| WO | WO 00/00095 A1 | 1/2000 |

\* cited by examiner

DEVICE WITH INFUSION HOLES FOR IMAGING INSIDE A BLOOD VESSEL

FIELD OF THE INVENTION

The field of the invention relates generally to devices for imaging inside a blood vessel and, more specifically, to imaging devices such as catheters capable of liquid infusion.

BACKGROUND OF THE INVENTION

Catheter imaging technology has long been recognized for its potential use in medical applications that involve visualizing the structure and conditions of a body. For example, catheter imaging technology may be used to locate anatomy, position diagnostic and therapeutic medical devices, and monitor surgery and surgical results.

Existing catheter imaging techniques include optical coherence domain reflectometers (OCDR), optical coherence tomography (OCT), acoustic imaging, intravascular ultrasound (IVUS), and optical triangulation.

Examples of utilizing OCDR to perform optical imaging are described in U.S. Pat. Nos. 5,459,570 and 5,321,501, both issued to Swanson et al., which are hereby incorporated by reference in their entirety.

An example of utilizing acoustic imaging is described in U.S. Pat. No. 4,951,677, issued to Crowley et al., which is hereby incorporated by reference.

Generally, these techniques involve emitting energy, such as light or sound, directed at a particular object and then detecting the energy's reflection or echo. Those skilled in the art will appreciate, however, that when using the techniques that emit high-frequency energy, such as near-infrared light or high-frequency ultrasound, in a body, blood may present a problem. This is due primarily to the presence of erythrocytes, or red blood cells (RBCs). The RBCs are of the size that interfere with short waves such as those of the high frequency energy. For example, in the case of OCT, blood may cause optical attenuation due to absorption and scattering.

In view of these limitations of conventional imaging catheters, an improved imaging device is needed.

SUMMARY OF THE INVENTION

An example imaging device includes an elongated member, having distal and proximal ends, an axis, a lumen along the axis, and an outer surface. The imaging device may be, for example, an imaging guidewire, imaging catheter, imaging probe, or imaging trocar. In an example embodiment of an improved device, an infusion hole or a plurality of infusion holes are defined along the axis of said elongated member between the lumen and the outer surface. The plurality of infusion holes may be tapered from the outer surface to the lumen. Further, the plurality of infusion holes may be angled outwardly toward the proximal end of the elongated member. Preferably, the improved imaging device infuses liquid efficiently and thoroughly into a blood stream while substantially preventing any radial jetting.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The components in the figures are not necessarily to scale, emphasis instead being placed upon illustrating the principles of the invention. Moreover, in the figures, like reference numerals designate corresponding parts throughout the different views. However, like parts do not always have like reference numerals. Moreover, all illustrations are intended to convey concepts, where relative sizes, shapes and other detailed attributes may be illustrated schematically rather than literally or precisely.

DETAILED DESCRIPTION OF THE PREFERRED EMBODIMENTS

Figure 1:
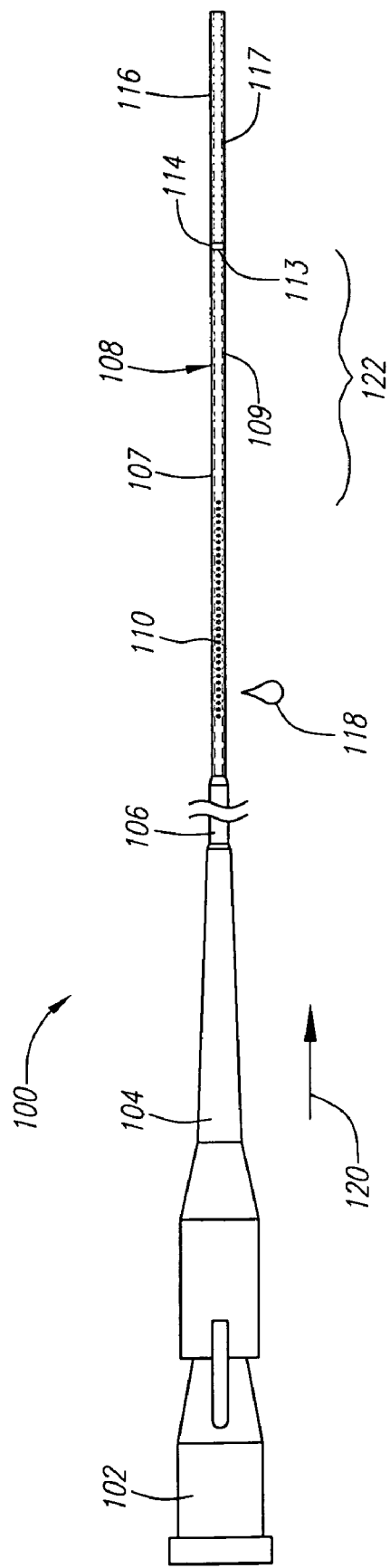
FIG. 1 is an illustration of a preferred embodiment of an improved imaging device in the form of a catheter.

FIG. 1 is an illustration of a preferred embodiment of an improved imaging device. In this example, the imaging device is an OCT imaging catheter 100. However, the imaging device can be an imaging guidewire, imaging probe, imaging trocar, or other other imaging devices. For the sake of convenience, the preferred embodiment is described as an imaging catheter 100, but this is not intended to exclude other imaging devices.

The imaging catheter 100 preferably includes an imaging window member 108, which is an elongated translucent polymer member having a lumen 109. The translucent property allows light to efficiently pass through the catheter wall 107, and thus, the imaging is performed through the imaging window member 108 at an imaging area 122. The distal end 113 of the window member 108 is adjacent to a guidewire exit 114 and a monorail tip 116. The monorail tip 116 has a lumen 117, which may accept a standard 0.0140" diameter guidewire (not shown), which guides the catheter 100 to the site of interest within a blood vessel.

A plurality of infusion holes 110 are positioned proximal to the imaging area 122, starting approximately 7 centimeters (cm) proximal to the distal end 113 of the window member 108, along the catheter wall 107. The infusion holes 110 extend between the catheter wall 107 and the lumen 109. Infusion liquid 118 is injected into the catheter 100, through the lumen 109, and forced out of the infusion holes 110 to displace and dilute the blood, which in turn, facilitates optimal imaging in the blood stream, as will be described in more detail below. By injecting a translucent liquid, such as a saline solution, into the blood stream, the RBC's are displaced and diluted so that more energy reaches the object unhindered. Preferably, the liquid 118 escapes the infusion holes 110 in a direction opposite the flow 120 of the blood stream.

Figure 3:
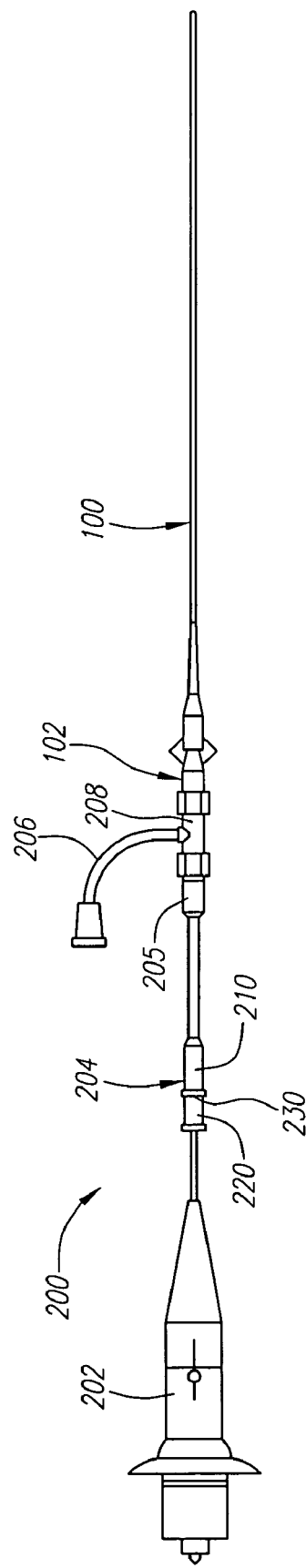
FIG. 3 is an illustration of a preferred embodiment of an improved imaging catheter assembly.

The proximal end of the window member 108 is coupled with a catheter stiffener extrusion 106, which in turn is coupled with a strain relief 104. The strain relief 104 advantageously helps reduce the chances of buckling the catheter stiffener extrusion 106 if the catheter 100 is pulled to one side during operation. The strain relief 104 is further coupled with a luer fitting 102, which provides a means to connect the catheter 100 with a luer adapter 208, an example of which is shown in FIG. 3.

Figure 2:
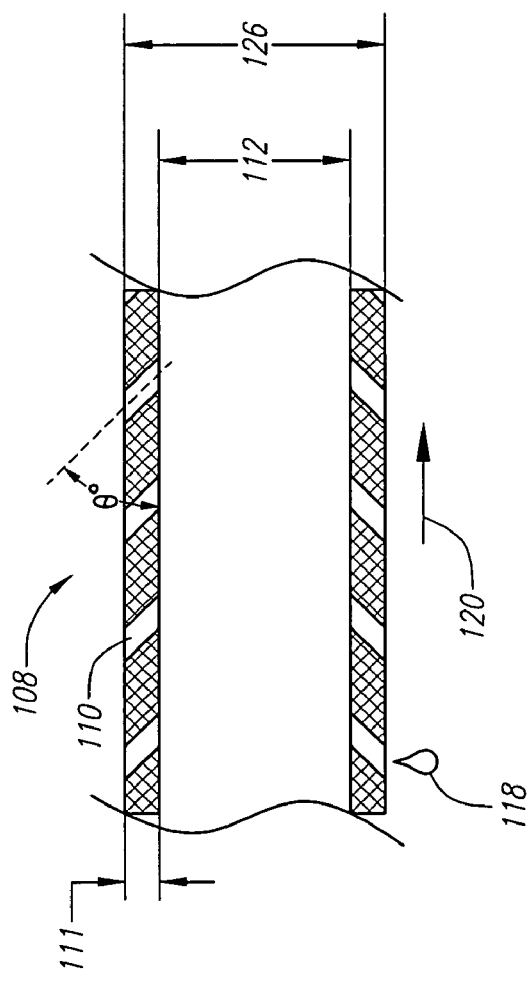
FIG. 2 is an illustration of a portion having infusion holes of the preferred embodiment of an improved imaging catheter.

FIG. 2 illustrates a portion of the imaging window member 108 having infusion holes 110. The infusion holes 110 are preferably smaller in diameter than the wall thickness 111 of the imaging window member 108. In this embodiment, the infusion holes 110 preferably have a diameter within the range of approximately 0.040 millimeters (mm) (0.0012 inches) and 0.30 mm (0.0118 inches). The infusion holes 110 are preferably spaced apart by a distance approximately in the range of 0.10 mm (0.0039 inches) and 0.90 mm (0.0354 inches). The infusion holes 110 may have a variety of shapes, e.g., the holes 110 may be circular, elongated, helical, and/or slots. The infusion holes 110 are preferably of a pattern to help retain the original bending rigidity and buckling resistance of the extrusion 106 before the infusion holes 110 were added.

With these example configuration and measurements, when infusion liquid 118 exits the holes 110, radial jets of liquid into the blood stream are substantially prevented. Multiple rows of infusion holes 110 may be utilized to deliver up to 4 milli-liters (mL) of infusion liquid 118 per second.

Further, the infusion holes 110 are preferably angled outward toward the proximal end of the catheter 100 at an angle $\theta°$, preferably approximately within the range of 15° to 60° from the axis of the catheter 100, which causes the flow direction of the infusion liquid 118 exiting the infusion holes 110 to be opposite the flow direction of the blood 120. Having the infusion liquid 118 flow against the direction of the blood flow 120 improves the mixing of the infusion liquid 118 and the blood, and thus providing a more thorough dilution in a more efficient manner.

As shown in FIG. 1, locating the infusion holes 110 proximal to the imaging area 122 provides two advantages: first, the infusion liquid 118 is carried distally by the blood flow 120, thus optimum dilution may occur around the imaging area; and second, false data or image artifacts may be created by the material discontinuity presented between the infusion holes 110 and the imaging window member 108. Of course, if desired, the location of the infusion holes 110 can be somewhere on the catheter other than proximal to the imaging area 122, such as distal to the imaging area 122. Further, the size, shape, spacing and configuration of the infusion holes 110 can take various forms.

For example, the diameter of the infusion holes 110 may be tapered with a smaller diameter at the inner surface 112 of the imaging window member 108 and a larger diameter at the outer surface 126 of the imaging window member 108. Further, the infusion holes 110 may be tapered at an angle to further reduce radial jetting.

FIG. 3 is an illustration of a preferred embodiment of an improved imaging catheter assembly. The assembly 200 includes an imaging catheter 100, such as the catheter 100 shown in FIG. 1, having its luer fitting 102 coupled with a luer adapter 208, which in turn, is coupled with another luer fitting 205, which forms a high-pressure seal. The luer adapter 208 includes a sidearm 206, which provides a port to attach a syringe or other high-pressure injection system (not shown), e.g., a MedRad injector commonly found in catheterization labs. With the sidearm 206, infusion liquid 118 may be injected into the catheter 100, through the lumen 109, and out the infusion holes 110.

The luer fitting 205 is coupled with a telescope assembly 204, which includes an inner tube 220 sliding within an outer tube 210 and a sliding seal 230 to prevent leakage. The telescope assembly 204 allows an imaging core assembly 312 (shown in FIG. 4) to slide axially inside the imaging catheter 100.

The telescope assembly is coupled with a catheter connector assembly 202, preferably with epoxy to create a sealed system that can handle high pressures without leakage.

Figure 4:
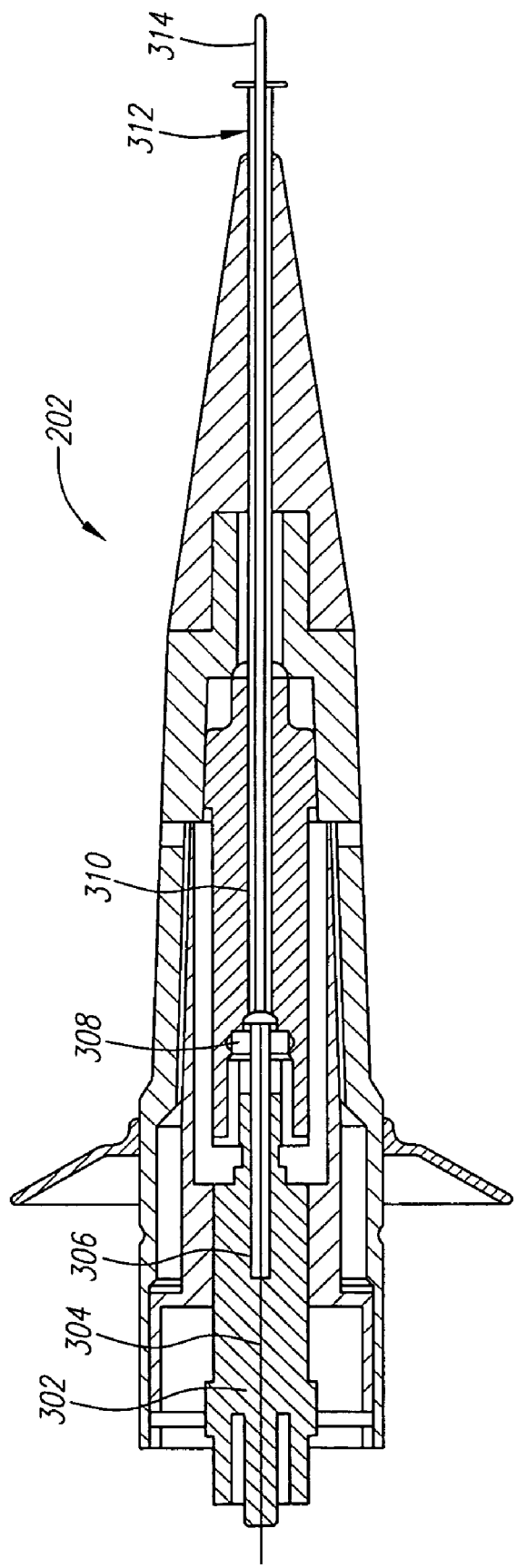
FIG. 4 is an illustration of a catheter connector assembly.

FIG. 4 is a detailed drawing of an example embodiment of the connector assembly 202, which receives an imaging core assembly 312. The imaging core assembly 312 preferably includes an optical fiber connector assembly 302, an optical fiber 304, a gland 306, a driveshaft 310, and a distal optics assembly 314. During operation, the imaging core assembly 312 rotates while the remaining components of the connector assembly 202 are held rotationally stationary. An O-ring 308 surrounds the gland 306 creating a high pressure seal. The O-ring 308 may be lubricated with a high vacuum grease (not shown) to improve its sealing capacity while reducing rotational friction. The gland 306 is bonded to the optical fiber connector 302 with epoxy.

The optical fiber connector 302 is adapted to be coupled with an optical fiber receptacle (not shown) within a drive motor assembly (not shown) to efficiently transfer light into the optical fiber 304 housed within the driveshaft 310. The catheter connector assembly 202 provides a secure attachment to the drive motor assembly (not shown), which provides the rotary drive to rotate the optical fiber connector 302, which in turn rotates the driveshaft 310 of the imaging core assembly 312.

Turning to a more detailed discussion of the mixture of the infusion liquid 118 and blood, in the case of an imaging catheter emitting light, e.g., an OCT catheter, the infusion liquid 118 is preferably translucent, as mentioned above. The liquid 118 should readily mix with the blood, and preferably should raise the refractive index of the liquid portion of the blood, known as the blood serum, to the refractive index of the RBCs. The RBCs typically have a refractive index of approximately 1.40, whereas the refractive index of blood serum is approximately 1.33.

A clear, low viscosity liquid with an index of refraction higher than 1.33 will raise the index of the liquid portion of blood closer to 1.40, and thus reduce the scattering of light that most severely attenuates the signal. One such preferable liquid is a saline solution.

However, saline carries little oxygen and other nutrients to the heart muscle, and thus angina may occur as a side effect of infusing saline into the blood stream. An alternative liquid for infusion is Dextran™. Upon investigation, Dextran™, when mixed with saline is a viscous liquid, which may require additional pressure to achieve the desired infusion rate. Another alternative liquid is Fluorosol™. Other infusion liquids 118 may also be used, such as those that carry a similar oxygen and nutrient load to that of blood.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

In the foregoing specification, the invention has been described with reference to specific embodiments thereof. It will, however, be evident that various modifications and changes may be made thereto without departing from the broader spirit and scope of the invention. For example, the reader is to understand that the specific ordering and combination of process actions described herein is merely illustrative, and the invention can be performed using different or additional process actions, or a different combination or ordering of process actions. For example, though the embodiment described above involves an OCT imaging catheter that emits light, the principles of the invention may readily applicable to an imaging catheter that uses a different form of energy, such as ultrasound. In other words, a person of skill in the art of catheter design and/or imaging may use a plurality of infusion holes 110 on a variety of imaging devices. As a further example, each feature of one embodiment can be mixed and matched with other features shown in other embodiments. Features and processes known to those of ordinary skill in the art of catheter design and/or imaging may similarly be incorporated as desired. For instance, the imaging device may include optional balloons, cauterization devices, cutting devices, drug delivery systems, and scopes. Additionally and obviously, features may be added or subtracted as desired. Accordingly, the invention is not to be restricted except in light of the attached claims and their equivalents.

What is claimed is:

1. An imaging device comprising:
   an elongated member having distal and proximal ends, an axis, and an outer surface;
   a lumen extending along the axis;
   a plurality of infusion holes defined in the elongated member, the plurality of infusion holes extending between the lumen and the outer surface, wherein the plurality of infusion holes have inner walls extending from the lumen to the outer surface that are angled outwardly toward one end of the elongated member; and
   an imaging window that is transparent to imaging energy and adapted to pass the imaging energy to an imaging area located distally to the plurality of infusion holes.

2. The imaging device of claim 1 wherein the diameter of the plurality of infusion holes tapers from the outer surface to the lumen.

3. The imaging device of claim 1 wherein the diameter of the plurality of infusion holes tapers decreasingly from the outer surface to the lumen.

4. The imaging device of claim 1 wherein the plurality of infusion holes are adapted to inject the liquid into the bloodstream in a direction that is opposite of the flow direction of the bloodstream.

5. The imaging device of claim 1 further comprising a tip coupled to the distal end of the elongated member, wherein the tip is adapted to receive a guidewire.

6. The imaging device of claim 1 wherein the plurality of infusion holes have a diameter within the range of approximately 0.040 millimeters to 0.30 millimeters.

7. The imaging device of claim 1 wherein the plurality of infusion holes are spaced apart by a distance approximately in the range of 0.10 millimeters to 0.90 millimeters.

8. The imaging device of claim 1 wherein the plurality of infusion holes are arranged in a plurality of rows.

9. The imaging device of claim 1 wherein the imaging device is capable of infusing liquid into a bloodstream such that the refractive index of the blood serum is raised.

10. The imaging device of claim 9 wherein said liquid is saline.

11. The imaging device of claim 9 wherein said liquid is Dextran™.

12. The imaging device of claim 9, wherein said liquid comprises an oxygen and nutrient load that is equal to blood disposed in the bloodstream.

13. The imaging device of claim 1 wherein the imaging device is a catheter.

14. The imaging device of claim 1 wherein the imaging device is an imaging guidewire.

15. The imaging device of claim 1 wherein the imaging device is an imaging probe.

16. The imaging device of claim 1 wherein the imaging device is an imaging trocar.

17. The imaging device of claim 1 further comprising an inflatable balloon.

18. The imaging device of claim 1 further comprising means to treat the blood vessel.

19. The imaging device of claim 1, wherein the inner walls of the infusion holes are angled between 15° to 60° with respect to the axis of the elongated member.

20. The imaging device of claim 1, wherein the plurality of infusion holes are tapered such that radial jetting is reduced when a liquid is passed through the infusion holes from the lumen to the outer surface.

21. The imaging device of claim 1, wherein the plurality of infusion holes are arranged in a pattern such that the elongated member comprises at least one of the bending rigidity or the buckling resistance of an otherwise similar elongated member that does not define infusion holes.

22. A catheter assembly comprising:
   an elongated member having distal and proximal ends and an outer surface;
   a lumen extending in and along the elongated member;
   a plurality of holes extending between the outer surface and the lumen of the elongated member, wherein the plurality of infusion holes have inner walls extending from the lumen to the outer surface that are angled outwardly toward one end of the elongated member;
   an imaging window that is transparent to imaging energy and adapted to direct the imaging energy to an imaging area located distally to the plurality of infusion holes;
   a sidearm adapter coupled with the proximal end of the elongated member, the sidearm adapter adapted to allow a liquid to be injected into the lumen of the elongated member; and
   a connector assembly coupled with the sidearm adapter.

23. The catheter assembly of claim 22 wherein the catheter assembly includes an imaging core assembly.

24. The catheter assembly of claim 22 wherein the catheter assembly is adapted to be coupled to an optical fiber receptacle.

25. A method for operating an imaging device within a bloodstream, having a flow direction, of a blood vessel of a body, the method comprising:
   inserting the imaging device into the blood vessel of the body, the imaging device having an elongated member with a central axis and an outer surface, a lumen extending along the axis, a plurality of infusion holes defined in the elongated member and extending between the lumen and the outer surface, wherein the plurality of infusion holes have inner walls extending from the lumen to the outer surface that are angled outwardly toward one end of the elongated member, and an imaging window that is transparent to imaging energy and adapted to pass the imaging energy to an imaging area located distally to the plurality of infusion holes;
   introducing a liquid into the imaging device;
   injecting the liquid through the infusion holes of the imaging device into the bloodstream of the blood vessel against the flow direction of blood in the vessel; and
   performing imaging through the imaging window of the imaging device.

26. The method of claim 25 wherein the liquid is translucent.

27. The method of claim 25 wherein the liquid is saline.

28. The method of claim 25 wherein the liquid is Dextran™.

29. The method of claim 25 wherein the liquid is Fluorosol™.

30. The method of claim 25 wherein the liquid has an index of refraction higher than the refractive index of blood serum.

31. The method of claim 25 wherein injecting the liquid raises the refractive index of blood serum within the bloodstream in the blood vessel.

32. The method of claim 25 wherein injecting the liquid raises the refractive index of the blood serum within the bloodstream to approximately 1.40.

33. The imaging device of claim 25, wherein injecting the liquid through the infusion holes of the imaging device into the bloodstream of the blood vessel against the flow direction of blood in the vessel comprises injecting the liquid such that the liquid does not flow radially from the infusion holes into the bloodstream.

* * * * *